United States Patent
Irvine et al.

(10) Patent No.: US 10,441,159 B2
(45) Date of Patent: Oct. 15, 2019

(54) SYSTEM AND METHOD FOR CLASSIFYING AND QUANTIFYING AGE-RELATED MACULAR DEGENERATION

(71) Applicant: The Charles Stark Draper Laboratory, Inc., Cambridge, MA (US)

(72) Inventors: John M. Irvine, Cambridge, MA (US); Richard Wood, Cambridge, MA (US); Nathan Lowry, Cambridge, MA (US); David Floyd, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 4 days.

(21) Appl. No.: 15/339,146

(22) Filed: Oct. 31, 2016

(65) Prior Publication Data

US 2017/0119243 A1  May 4, 2017

Related U.S. Application Data

(60) Provisional application No. 62/248,807, filed on Oct. 30, 2015.

(51) Int. Cl.
| | |
|---|---|
| G06K 9/00 | (2006.01) |
| A61B 3/00 | (2006.01) |
| A61B 3/10 | (2006.01) |
| G06K 9/62 | (2006.01) |
| G06T 7/00 | (2017.01) |

(52) U.S. Cl.
CPC .......... *A61B 3/0025* (2013.01); *A61B 3/102* (2013.01); *G06K 9/00617* (2013.01); *G06K 9/6286* (2013.01); *G06T 7/0012* (2013.01); *G06K 2209/05* (2013.01); *G06T 2207/10101* (2013.01); *G06T 2207/20076* (2013.01); *G06T 2207/20084* (2013.01); *G06T 2207/30041* (2013.01)

(58) Field of Classification Search
CPC .. A61B 3/0025; A61B 3/102; G06K 2209/05; G06K 9/00617; G06K 9/6286; G06T 2207/30041; G06T 7/0042
See application file for complete search history.

(56) References Cited

PUBLICATIONS

Savastano, Maria Cristina, et al. "Differential vulnerability of retinal layers to early age-related macular degeneration: evidence by SD-OCT segmentation analysis." Investigative ophthalmology & visual science 55.1 (2014): 560-566. (Year: 2014).*

* cited by examiner

*Primary Examiner* — Nirav G Patel
(74) *Attorney, Agent, or Firm* — Christopher J. McKenna; Foley & Lardner LLP

(57) ABSTRACT

The present disclosure describes a system and method to classify optical coherence tomography (OCT) images. The present system can classify OCT images without first segmenting the retina tissue. The system can generate one or more profiles from vertical transects through the OCT images. The system can identify image statistics based on the one or more profiles. The system's classifier can then classify the OCT images based on the identified image statistics.

18 Claims, 5 Drawing Sheets

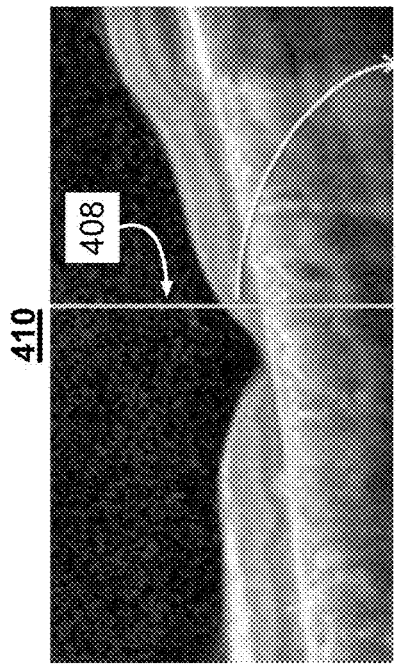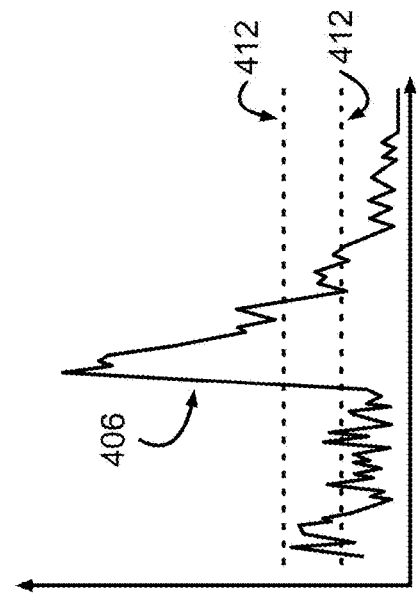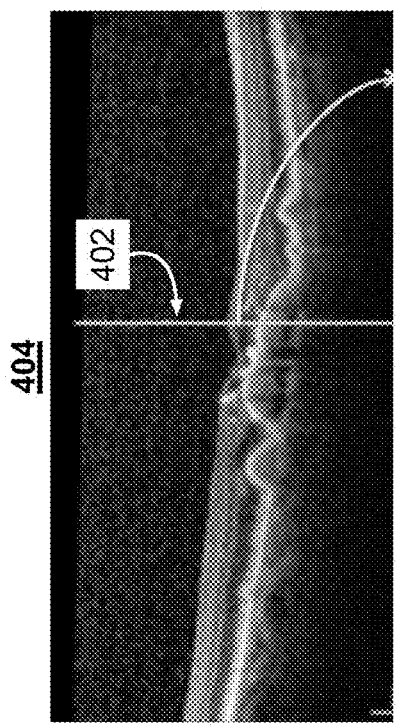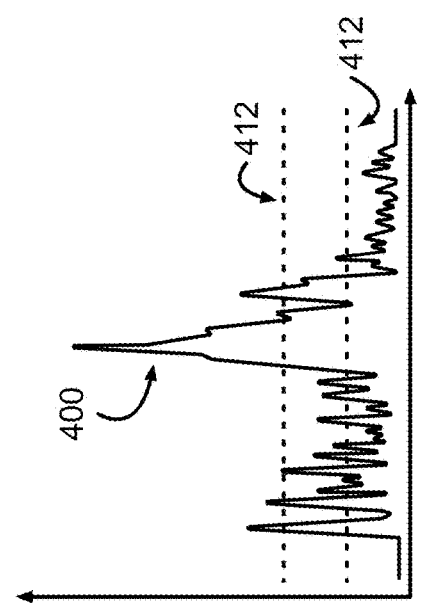
FIG. 4A
FIG. 4B

SYSTEM AND METHOD FOR CLASSIFYING AND QUANTIFYING AGE-RELATED MACULAR DEGENERATION

CROSS-REFERENCE TO RELATED APPLICATIONS

This application claims priority to U.S. Provisional Patent Application No. 62/248,807 filed on Oct. 30, 2015, which is herein incorporated by reference in its entirety.

BACKGROUND OF THE DISCLOSURE

Optical Coherence Tomography (OCT) is an optical imaging technology that can generate non-invasive, real time, high-resolution cross sectional images of tissue structures. In many implementations, the images captured by OCT device have a micrometer resolution.

OCT devices can generate cross-sectional images of a patient's retina—providing a view of the different retinal layers. The cross-sectional images (also referred to as slices) can be useful in the diagnosis of retinal diseases and also in measuring the efficacy of treatments. In some cases, cross-sectional images near predetermined ocular structures, such as the fovea, can be the most important when making clinical decisions based on the cross-sectional images. The fovea can be important because the fovea includes a concentration of cones and rods.

SUMMARY OF THE DISCLOSURE

In some implementations, each of the layers of an OCT slice needs to be identified for diagnostic purposes. The system and methods described herein can automatically segment selected OCT images of both diseased and healthy retina layers. Features can be calculated for the segmented layers in order to perform procedure outcome prediction, efficacy and re-dosing analysis, and other clinical analysis.

According to one aspect of the disclosure, a system of the present disclosure includes one or more processors and a memory. Execution of the instructions stored in the memory can cause the one or more processor to retrieve, from the memory, an OCT image of retina tissue. Execution of the instruction can also cause the one or more processors to determine a location of a fovea in the OCT image, and extract a transect from the OCT image a predetermined distance from the fovea. The transect can include an array of intensity values through the retina tissue of the OCT image. Execution of the instructions can also cause the one or more processors to generate a profile for the transect. The profile for the transect can include at least one image statistic of the transect. The system can classify the OCT image responsive to the profile of the transect.

In some implementations, the system can preprocess the OCT image. Preprocessing the OCT image can include at least one of down-sampling, de-noising, filtering or flattening the OCT image. The OCT image can be filtered a Frangi filter.

In some implementations, the system is configured to identify an outline of the of the retina tissue, calculate a derivative of the outline, and determine a location of a minimum of the derivative. The minimum can be marked as the center of the fovea.

In some implementations, the system can be configured to extract a plurality of transects from the OCT image. The system can generate the profile responsive to each of the plurality of transects. In some implementations, the system can generate a respective profile for each of the plurality of transects.

In some implementations, the image statistics can include a number of times the profile crosses at least one threshold. The system can classify the OCT image with at least one of a linear discriminant analysis (LDA), a k-nearest neighbor based algorithm, or a support vector machine.

According to another aspect of the disclosure, a method can include retrieving, from a memory, an OCT image of retina tissue. The method can also include determining a location of a fovea in the OCT image. The method can include extracting a transect from the OCT image. The transect can include an array of intensity values through the retina tissue of the OCT image. The method can also include generating a profile for the transect. The profile for the transect can include at least one image statistic of the transect. The method can include classifying the OCT image responsive to the profile of the transect.

In some implementations, the method can include preprocessing the OCT image. Preprocessing can include at least one of down-sampling, de-noising, filtering or flattening the OCT image. The filter can be a Frangi filter.

In some implementations, the method can include identifying an outline of the of the retina tissue, calculating a derivative of the outline, and determining a location of a minimum of the derivative.

In some implementations, the method can include extracting a plurality of transects from the OCT image. The method can include generating the profile responsive to each of the plurality of transects. The method can also include generating a respective profile for each of the plurality of transects.

In some implementations, the method can include determining a number of times the profile crosses at least one threshold. In some implementations, the method can include classifying the OCT image with at least one of a linear discriminant analysis (LDA), a k-nearest neighbor based algorithm, or a support vector machine.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale; emphasis instead being placed upon illustrating the principles of the teachings. The drawings are not intended to limit the scope of the present teachings in any way. The system and method may be better understood from the following illustrative description with reference to the following drawings in which:

FIGS. 4A and 4B illustrate example profiles generated from example OCT images using the system illustrated in FIG. 1.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

As an overview, the present disclosure describes systems and methods for classifying OCT images. The system can process OCT images of the retina to provide support concerning the diagnosis, trajectory, and response to therapy for wet and dry Age-related Macular Degeneration (AMD) and other eye related diseases. The system can calculate image-derived features that can form the basis for biomarkers (e.g., a set of objective measures). The biomarkers can be used to characterize and quantify the AMD and other diseases. In some implementations, the system can perform accurate classification of wet AMD OCT images without the need for first segmenting the OCT image. Disease pathology can make it difficult to delineate between the different tissue layers of the eye—making segmentation difficult. Accordingly, classifying the OCT image without the need for first segmenting the image can provide increased classification results with respect to methods that first segment the OCT image.

The system can classify OCT images by extracting vertical transects (also referred to as transects) from the OCT image. The system can convert the transects into profiles that are used in the classification of the OCT image. Because the system can operate without first segmenting the OCT image, the system can operate successfully on a broader range of images and exhibits greater robustness to image quality.

Figure 1:
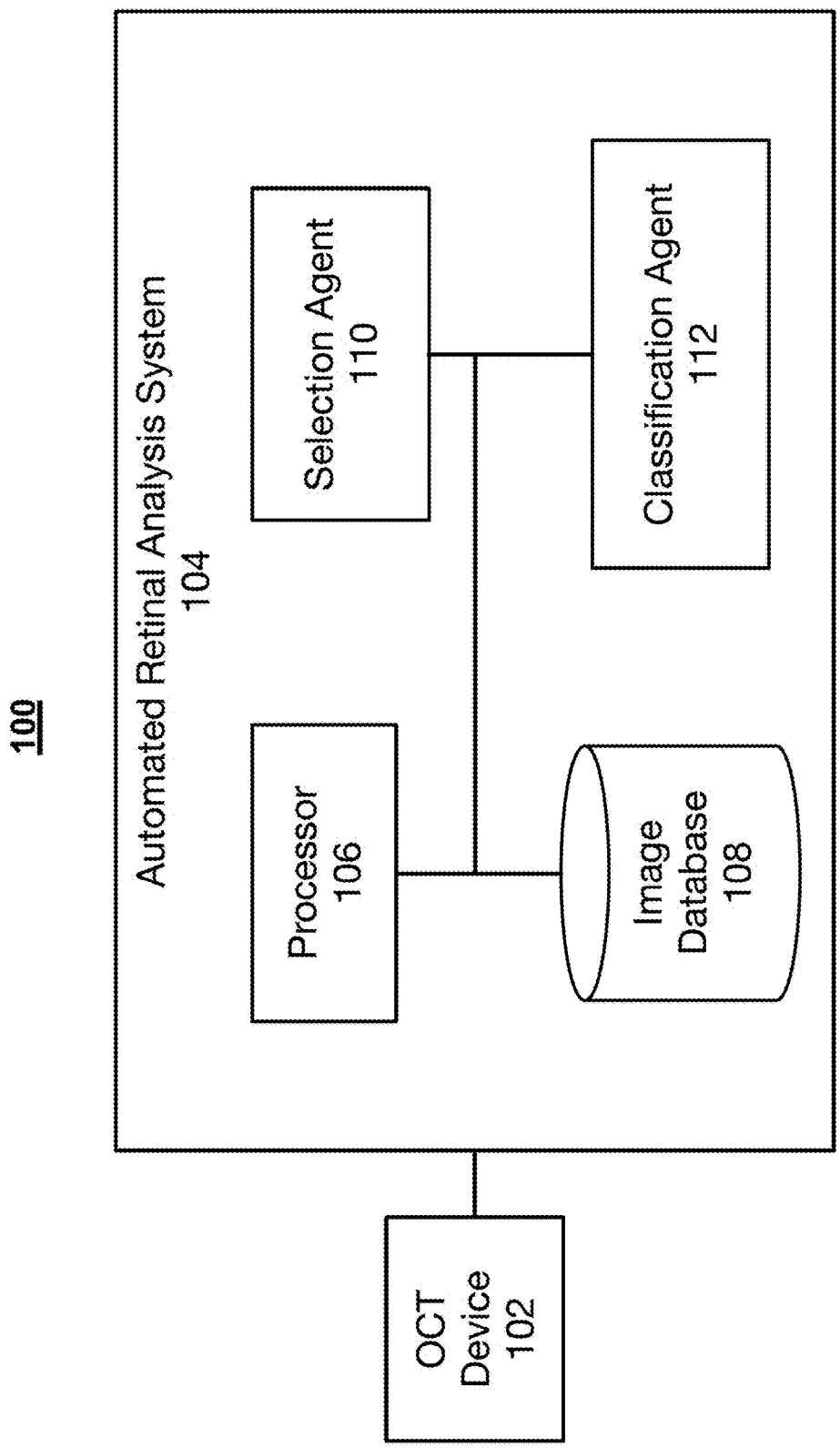
FIG. 1 illustrates an example system for analyzing retinal images.

FIG. 1 illustrates an example system 100 for analyzing retinal images. The system 100 includes an OCT device 102 that is coupled to an automated retinal analysis system (ARAS) 104. The ARAS 104 includes at least one processor 106 and an image database 108. The ARAS 104 also includes a selection agent 110 and a classification agent 112.

The OCT device 102 of the system 100 includes one or more OCT devices 102 that generate the OCT images. The OCT device 102 is a device configured to measure the thickness of tissue, such as the retinal thickness and the retinal nerve fiber layer thickness. The OCT device 118 can be any type of OCT device that generates an OCT image. In some implementations, the OCT device 102 is located remotely from the ARAS 104. For example, images are captured by the OCT device 102 and transferred to the ARAS 104 over a network, such as the internet, or physically via removable media. In other implementations, ARAS 104 is located local to the OCT device 102 or may be a component of the OCT device 102 itself. In general, the OCT device 102 can generate a plurality of A-scans across the retina or other tissue region of interest. Each A-scan measures a time-delay of light reflected from a specific point location on the retina. Neighboring A-scans are laterally combined to create cross-sectional images of the retina. The laterally combined A-scans are referred to as B-scan images (or generally, OCT images or OCT slices). A total OCT scan includes generating a plurality of A-scans along both an x axis and a y axis over a region of interest. The A-scans along one of the axes are laterally combined to form a plurality of cross-sectional OCT slices. For example, and assuming a 256×256 grid of A-scans, the A-scans at location (1, y) are laterally combined to form a first B-scan, the A-scans at location (2, y) are laterally combined to form a second B-scan, and so forth until the A-scans at location (256, y) are laterally combined to form a 256th B-scan. The A-scans can be laterally combined along the x or y axis.

The methods described herein are executed by the processor 106 of the ARAS 104. In some implementations, the processor 106 of the ARAS 104 is a processor of a general purpose computer executing software. In other implementations, the functions performed by the ARAS 104 are performed by special purpose logic circuitry, such as a field programmable gate array of application specific integrated circuit. The processor 106 can be a processor of the OCT device 102.

The ARAS 104 includes an image database 108. The image database 108 is configured to store OCT images captured by the OCT device 102. For example, OCT images are captured by the OCT device 102, transferred to the ARAS 104, and then stored in the image database 108 for later analysis. The image database 108 can include or be stored on any type of computer readable medium such a hard drive, solid state drive, or other forms of volatile or non-volatile memory. In some implementations, memory on which the image database 108 is stored also stores computer executable instructions that are executed by the processor 106 to perform the methods described herein.

The ARAS 104 of the system 100 is configured to automatically select near- and through-fovea OCT images. The near- and through-fovea OCT images can be of higher clinical relevance than compared to OCT images not near the fovea. Accordingly, the near- and through-fovea OCT images can be selected prior to making diagnosis or other clinical judgments. The selection of the OCT images can be made by the selection agent 110 of the ARAS 104. The selection agent 110 can select the near- and through-fovea containing OCT images from the image database 108. The selection agent 110 includes processor executable instructions executed by the processor 106 or specialty purpose logic circuits to identify near-fovea and fovea containing OCT images provided to the ARAS 104. The selection agent 110 can use one or more 2D based algorithms to analyze the OCT images to locate near- and through-fovea OCT images. In some implementations, the selection agent 110 can use one or more 3D based algorithms to analyze the OCT images to locate near- and through-fovea OCT images. In some implementations, the 2D based algorithms and the 3D based algorithms can operate independently of one another, and in other implementations, they can operate together in a hybrid fashion to identify near- and through-fovea OCT images.

In some implementations, the selection agent 110 can select through-fovea OCT images by computing a difference of neighboring points of a line outlining the retina tissue surface in each of the OCT images (e.g., a line tracing the border of the retina tissue). The difference of neighboring points of a line outlining the retina tissue surface can generally be referred the first difference line. In some implementations, the computed difference includes calculating the difference between neighboring points of the first difference line. The resulting line can be referred to as the second difference line. In many OCT images, the fovea is located at a dip in a line tracing the top layer of retinal tissue. In some implementations, the fovea is located in a relatively high curvature region of the retinal tissue. Taking the first (and second) difference enables the dip in the retinal tissue boundary line that is indicative of the fovea to be detected in regions of high curvature. In some implementations, the first and second differences are smoothed with a moving average filter to reduce jitter present in the line tracing the top layer of retinal tissue.

In some implementations, the selection agent 110 selects the through-fovea OCT images from the stored OCT images by calculating a 2nd difference between neighboring points of a line outlining the retina tissue. The OCT images containing a 2nd difference that falls below a predetermined threshold are selected as candidate OCT image likely to include the fovea. Valleys in the tissue, such as the fovea, can have a 2nd difference line below 0. Natural undulations in the surface of the retinal tissue other than the fovea can also result in a 2nd difference line below 0. Setting a threshold substantially below 0 can enable discrimination between OCT images that include natural undulations and OCT images that include the fovea. In some implementations, the threshold is manually set by a user of the system responsive to the patient's pathology, and in other implementations, the threshold is automatically set. For example, the threshold can be set to be one standard deviation above the mean of the 2nd difference line. The selection agent 110 can save the OCT images where the 2nd difference line crosses below the threshold as candidate OCT images or flag the original OCT images in the image database 108.

In some implementations, if the selection agent 110 saves multiple OCT images as candidate OCT images, then the selection agent 110 can selected one of the OCT image among the candidate OCT images as the OCT image for further analysis and classification. For example, the selection agent 110 can select OCT image passing through the center of the fovea. The OCT image passing through the center of fovea can contain the lowest overall point in its respective 2nd difference line when compared to 2nd difference lines of the other candidate OCT images. In some implementations, the selection agent 110 identifies the remaining candidate OCT images as near-fovea OCT images.

Referring to FIG. 1, the ARAS 104 also includes the classification agent 112. The classification agent 112 can classify the OCT images as normal images, dry AMD images, or wet AMD images. As an overview, the classification agent 112 can process the OCT image selected by the selection agent 110 to characterize and quantize wet and dry AMD. The classification agent 112 can also perform image-based treatment predictions for patient outcomes with wet AMD. The classification agent 112 can also perform prediction of visual acuity scores using features derived from the OCT images. In some implementations, the classification agent 112 can exploit the statistical properties of the A-scans of the OCT imagery to compute relevant features for classification and prediction. The classification agent 112 can classify the OCT images without first segmenting the OCT image. As segmentation is often difficult in the OCT images of patients with AMD, not segmenting the image can make the classifications made by the classification agent 112 more robust to issues of image quality, the type of OCT imaging device, and pathology that can arise in severe AMD cases.

As described further below, the classification agent 112 can classify the OCT image using vertical transects through the OCT image. The classification agent 112 can identify statistical features in the vertical transects, such as run length and the number of crossings of one or more predetermined thresholds.

Figure 2:
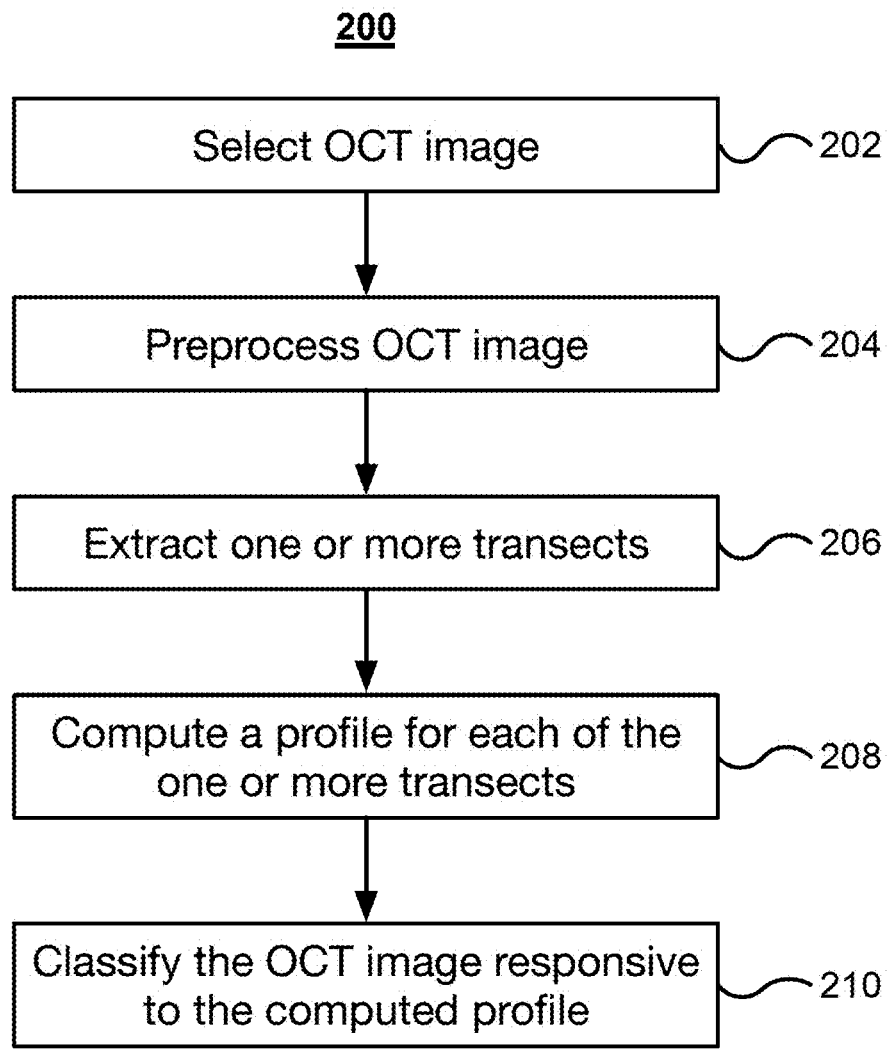
FIG. 2 illustrates a flow chart of an example method for classifying OCT images using the system illustrated in FIG. 1.

FIG. 2 illustrates a flow chart of an example method 200 for classifying OCT images. The method 200 includes selecting an OCT image (step 202). The OCT image can be preprocessed by the system (step 204). One or more transects can be extracted from the OCT image (step 206). Profiles can then be computed for the transects (step 208). The OCT image can then be classified responsive to the profiles (step 210).

As set forth above, the method 200 can include selecting an OCT image (step 202). In some implementations, an OCT scan of a patient's eye is captured and stored in the system's image database. The OCT scan can include a plurality of A-scans, which are used to generate a plurality of B-scans. As described above, the selection agent of the ARAS can select near- and through-fovea OCT images from the OCT images captured of the patient's retina. In some implementations, a medical professional selects and supplies a through-fovea OCT image (or other OCT image) to the system for classification.

The method 200 can also include preprocessing the OCT image (step 204). In some implementations, preprocessing the OCT image can include normalizing the OCT image. For example, the brightness of each pixel in the OCT image can be normalized into a range between 0 and 1 by dividing the brightness value of each pixel by the OCT image's maximum brightness value. The preprocessing step can also include de-noising the OCT image. In some implementations, de-noising can be implemented by applying a Gaussian filter to the OCT image. In other implementations, the de-noising is implemented by applying a median filter, through total variation de-noising, or by applying a shock filter. In some implementations, the Gaussian filter uses a window between about 5 and about 20 pixels, about 5 and about 15 pixels, or about 5 pixels and about 10 pixels to smooth the OCT image. The preprocessing step can also include resampling (e.g., down or up sampling) the OCT image.

The preprocessing step 204 can also include rotating and/or cropping the OCT image. For example, the classification agent can identify the inner limiting membrane (ILM) and determine if the ILM is substantially horizontal. The classification agent can rotate the OCT image to make the ILM substantially horizontal. In some implementations, the OCT image can be rotated to make the tissue near the fovea substantially horizontal.

In some implementations, the preprocessing step 204 can include flattening the OCT image. As the OCT image is a cross-sectional image of the back portion of the eye, the retinal tissue is curved and can form a convex shape in the OCT image. Flattening the image corrects for the image angle and the curved shape of the eye. Flattening the image linearizes the tissue within the image. In some implementations, the OCT image is flattened by finding a convex hull of the OCT image using a binary mask. The bottom of the convex hull corresponds to the curvature of the eye. The bottom of the convex hull is flattened to flatten the curvature of the retinal tissue.

In some implementations, the preprocessing step 204 can include filtering the OCT images. In some implementations, OCT images can be with poor quality can be excluded from steps 206-210 because they may create false measurements in the subsequent steps. In some implementations, the OCT images with poor quality are enhanced through filtering and still used in the subsequent steps of the method 200. The ARAS can determine the quality of the OCT image by measuring the sharpness, signal to noise ratio, valid area (e.g., area of the OCT image including tissue), noise area (e.g., area of the OCT image including noise), orientation, noise above the ILM, or any combination thereof in the OCT image.

For OCT images exhibiting higher levels of noise or other decrements in image quality, the ARAS can apply wavelet and Frangi filtering. A Frangi filter is a filter that is used for vessel enhancement. Applying the Frangi filter to OCT imagery can reduce the variability within the layers of the retina. The Frangi filter can use the eigenvectors of a Hessian matrix to determine areas within the OCT image that are likely to be contain vessel (or tubular like) structures. The eigenvalue analysis of the Hessian matrix can determine the principal directions in which the local second order structure of the image can be decomposed, which can give the direction of the smallest curvature along an edge. In some implementations, the Frangi filter can detect edges within the OCT image.

Figure 3B:
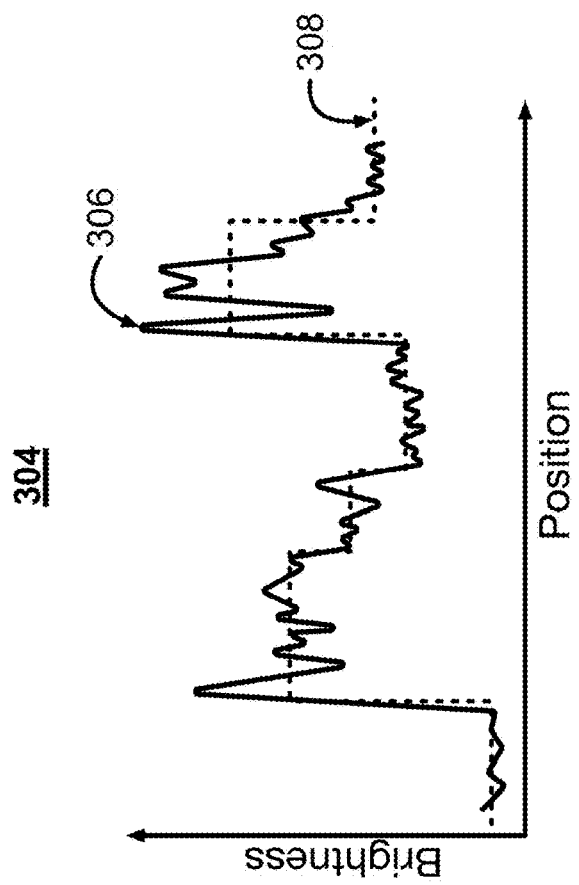
FIG. 3B illustrate the vertical transect generated at location indicated in FIG. 3A.
Figure 3A:
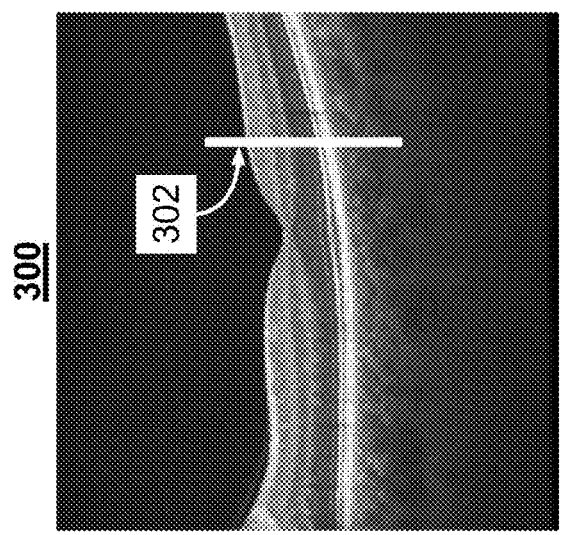
FIG. 3A illustrates an OCT image indicating the location of a vertical transect.

Referring to FIG. 2 and FIGS. 3A and 3B, the method 200 can also include extracting one or more transects (step 206). In some implementations, extracting the transects can include identifying the pixels of the OCT image that correspond to the transects. FIG. 3A illustrates an example OCT image 300 with a vertical transect taken from location 302. FIG. 3B illustrate the vertical transect 304 generated at location 302 in FIG. 3A. The vertical transect 304 is illustrated as a plot of the values 306 (solid line) or a spline plot 308 (dashed line), which is a stepwise function that approximates the plot of the values 306. The transect 304 can be an array of intensity values from each of the pixels located at the location 302. For example, if the OCT image is a 256×256 image and the horizontal location of the transect is x=150, the array that forms the transect can be the intensity values of the pixels at [(1, 150), (2, 150), . . . , (256, 150)]. In some implementations, the method 200 can include extracting a plurality of transects. For example, a first transect can be extracted from the center of the fovea and then additional transects can be extracted a set internal from the center of the fovea. In some implementations, between about 50 and about 5, between about 5 and about 40, between about 5 and about 20, or between about 5 and about 10 transects are extracted. In some implementations, transects closer to the fovea are weighted greater than transects further from the fovea.

Referring to FIG. 2, the method 200 can also include computing a profile for each of the one or more transects (step 208). In some implementations, and referring to FIGS. 3A and 3B, the vertical transect 304 is the A-scan located at the location 302. Without modification, the A-scan from at the location of the OCT image (or B-scan) can be used as the profile. In other implementations, the classification agent can perform one or more processing steps on the A-scan to generate the profile for the vertical transect. In some implementations, the classification agent can average one or more A-scans on either side of the location of the transect to generate the profile for the transect location. For example, between about 1 and about 25, about 1 and about 20, about 1 and about 10, or about 1 and about 5 A-scans can be averaged together to generate the vertical transect 304. In some implementations, the A-scans can be smoothed with, for example, a moving average filter to smooth the profile and reduce noise effects.

The method 200 can also include classifying the OCT image responsive to the computed profiles (step 210). In some implementations, the classification agent computes image statistics for each of the profiles. In some implementations, the image statistics include calculating a number of times the profile crosses one or more thresholds. FIG. 4A illustrates the profile 400 generated at location 402 in the OCT image 404. The OCT image 404 is from a patient with wet AMD. FIG. 4B illustrates the profile 406 generated at location 408 in the OCT image 410. The OCT image 410 is from a control patient without wet AMD. The plots of the profiles illustrated in FIGS. 4A and 4B each include two thresholds 412.

In some implementations, the classification agent can classify the OCT images responsive to the number of times the profile crosses one or more of the thresholds. The threshold can be placed at about the $25^{th}$, $50^{th}$, $75^{th}$ percentile, or any combination thereof. For example, in FIGS. 4A and 4B, the thresholds 412 are placed at the $25^{th}$ and $50^{th}$ percentiles. In some implementations, the image statistics can include measuring the shortest and longest lengths of the profile that are above or below each of the thresholds. In some implementations, the image statistics can be calculated responsive to a single profile and in other implementations the image statistics are responsive to a combination of the profiles generated at set internals from the fovea. When a plurality of profiles is used, the image statics can include a weighted means and standard deviation of the threshold crossings across each of the profiles. In some implementations, the weighting of the profiles is responsive to the profile's distance to the fovea. Each of the profiles can have equal weighting. The classification agent can then classify the image statistics using liner discriminant analysis, k-nearest neighbor, or support vector machines.

The ARAS can also use the profiles generated during the method 200 to estimate visual acuity and predict treatment outcomes using the pre-treatment OCT images. Examples of classifying the OCT images, estimating visual acuity, and predicting treatment outcomes are illustrated in the below examples.

Example 1: OCT-Based Classification of Subjects

In this example, the system described herein classified and assigned patient conditions based on the features (e.g., image statistics) extracted from the OCT images. The data set provided to the system included OCT images from healthy patients (e.g., patients with no known retinal diseases), dry AMD patients, and wet AMD patients. The data set includes approximately 75 patients. As described above, the features extracted from the OCT imagery can be statistical characteristics of the retina. In some implementations, a healthy eye can include a retina with layered structure that exhibit well-behaved patterns. Various chaotic behaviors of the layers of the retina can indicate the deterioration of the retina associated with Wet or Dry AMD.

In the present example, the classification agent used linear discriminant analysis (LDA), k-nearest neighbor, and support vector machines to classify the OCT images. In other implementations, the classification agent can use other classification algorithms including, but not limited to, neural networks, random decision forests, and deep learning. The discrimination analysis was performed on image features generated from the profiles extracted from the OCT images. In this example, the image features included the number of times the profiles crossed thresholds set at the 25th and the 50th percentile of the OCT images' brightness.

Figure 5:
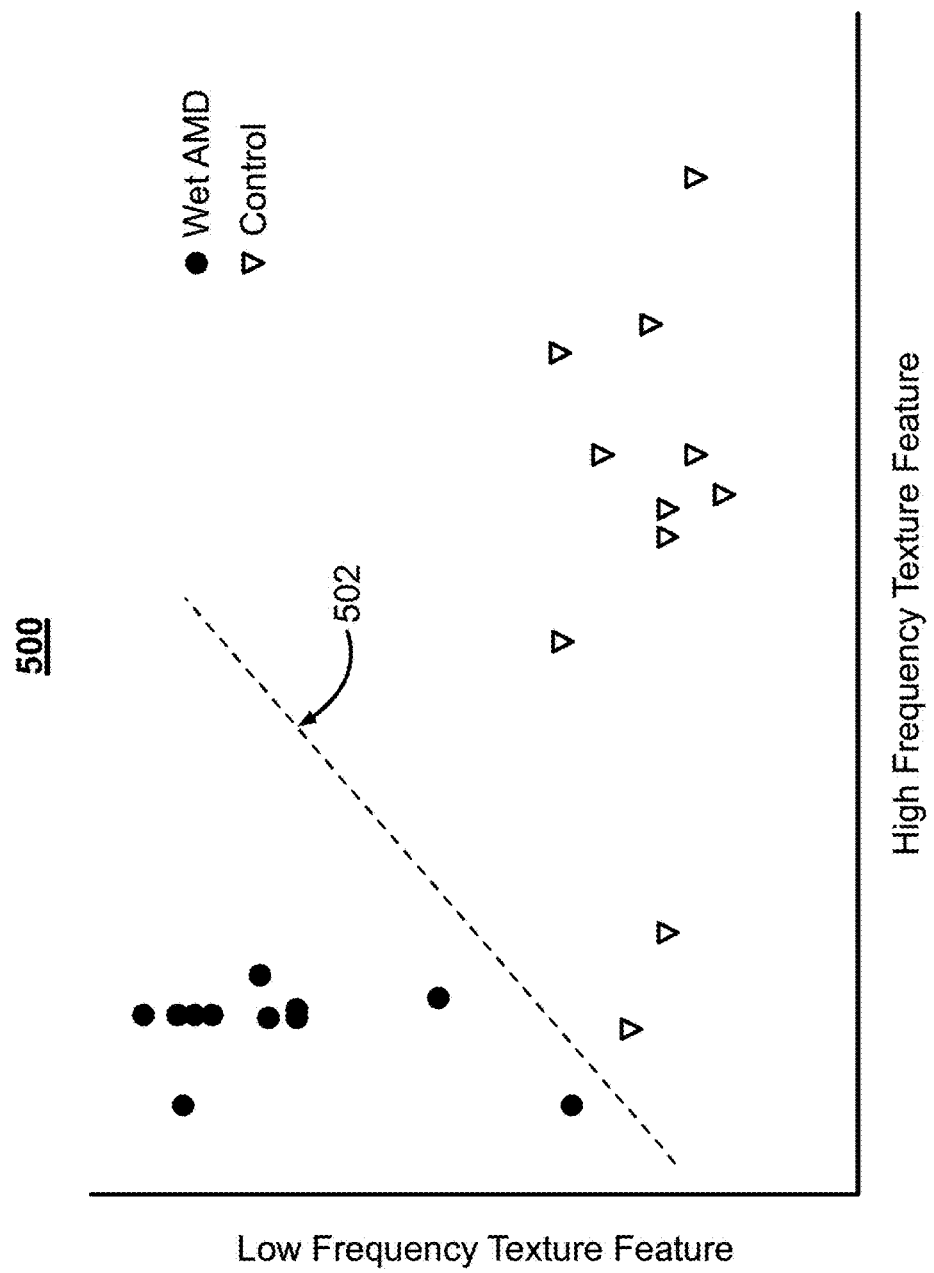
FIG. 5 illustrates a plot of the separability between the wet AMD and control subjects using the system illustrated in FIG. 1.

FIG. 5 illustrates a plot 500 of the separability between the wet AMD and control subjects. The classification analysis performed by the classification agent indicates a separability of Wet AMD from other conditions, including Dry AMD and healthy retinas. For example, the wet AMD points (filled circles) and control points (open triangles) lie on either side of the boundary line 502. The probability of correct classification of was 95.7%, as determined from cross validation using LDA. The stepwise forward selection identified two features which quantified the weighted average of the number of crossings for the 25th and 75th percentiles. The plot 500 illustrates the relationship between the number of crossings of the $25^{th}$ percentile (labeled as the low frequency texture feature) and the $75^{th}$ percentile (labeled as the high frequency texture feature). As illustrated in the plot 500, the image features from the wet AMD images had a greater number of low frequency threshold crossings and a lower number of high frequency threshold crossings. In contrast, the control images had a lower number of how frequency threshold crossings and a higher number of high frequency threshold crossings. Experiments with the system provided similar results with other features sets.

Example 2: OCT-Based Estimate of Visual Acuity

The system can also predict visual acuity scores. The system can include a statistical model that can use OCT image features to predict best corrected visual acuity (BCVA) scores. The linear model can predict the log(MAR) score for visual acuity based on features derived from the OCT imagery. Table 1 illustrates two explanatory variables used by the system to predict visual acuity. The specific image features in this case are the weighted mean number of crossings of the 75th percentile and the relative frequency of the number of crossings (e.g., the histogram of the frequency of crossings) for the 25th percentile. The system generates a regression model using the specific image features generated from OCT images from patients with known visual acuity scores. Generating the specific image features of patients with unknown visual acuity scores using the above-described method, the image features can be provided to the regression model to estimate the visual acuity score of the patient.

TABLE 1

Regression Model for Predicting BCVA

| Image Feature | Coefficient | Std. Error | T-statistic | P-value |
| --- | --- | --- | --- | --- |
| (Constant) | 1.471 | 0.164 | 8.990 | 0.000 |
| Transect_Cross_75 | −0.122 | 0.012 | −10.399 | 0.000 |
| Histogram_2 | 0.007 | 0.003 | 2.382 | 0.027 |

Example 3: OCT-Based Prediction Using Pre-Treatment Images

In some implementations, the present system is also configured to predict patient responses to therapy. For example, using the pre-treatment OCT imagery, the system can predict whether a patient's vision score will improve, remain approximately the same, or get worse following a specific treatment. The prediction relies on the features extracted (as discussed above) from the OCT imagery acquired prior to treatment.

In the present example, the patients were examined during office visits at intervals over the treatment cycle. During each visit, patients performed a visual acuity test and the results were recorded. Patients exhibiting a substantial improvement in the visual acuity test were labeled as getting better, patients exhibiting no change or small improvements were labeled as "not worse." Finally, patients who experienced a decrease in the visual acuity score were labeled as getting worse.

Of the available data, covering 45 patients in total, imagery data was available for 35 patients. However, only 11 patients were available with both pre- and post-injection images and visual acuity tests. Two binary classifiers were tested: one distinguished between subjects that got worse vs. those who did not. The second classifier distinguishes between those who got better and those who did not. Thus, the two classifier analyses differed in the handling of the group that showed little or no improvement.

The method of the present example was similar to the method 200 described above and included applying the filtering described above, extracting features from the filtered images, and performing the classification analysis. Using the 11 patients identified in Table 2, the system performed both cross validation and leave-one-out analysis. In the cross-validation, a random selection of 5 patients were assigned to the test set and the other 6 patients were the training samples. Correct classification using this very small training set was still significantly better than chance and averaged around a correct classification rate of 60%. Performing a leave-one-out analysis yielded a correct classification rate on approximately 95%.

Even with the limited data set, the results indicate that valuable information can be extracted from the OCT imagery using the methods described herein. The system, which does not rely on traditional image segmentation techniques, offered effective methods for characterizing retinal disease and predicting treatment outcomes.

TABLE 2

Summary of Patient Data for Wet AMD Treatment

| Patient ID | Pre-injection Score | Post-injection Score | Label (2 class) Worse/ Not Worse | Label (2 class) Better/ Not Better |
| --- | --- | --- | --- | --- |
| 26794(OS) | 20/70 − 1 | 20/40 | Not worse | Better |
| 11111912(OS) | 20/30 | 20/30 | Not worse | Not Better |
| 11315(OD) | 20/40 | 20/50 | Worse | Not Better |
| 53735(OD) | 20/100 | 20/200 | Worse | Not Better |
| 53735(OS) | 20/40 − 2 | 20/30 + 2 | Not worse | Better |
| 26794(OD) | 20/25 − 2 | 20/25 | Worse | Not Better |
| 74208(OD) | 20/70 − 2 | 20/60 | Not worse | Better |
| 24237(OD) | 20/25 + 2 | 20/25 − 2 | Not worse | Better |
| 12780(OD) | 20/30 + 2 | 20/25 | Not worse | Better |
| 33854(OD) | 20/200 | 20/60 | Not worse | Better |
| 23781(OD) | 20/40 | 20/50 | Worse | Not Better |

The disclosed system and methods may be embodied in other specific forms without departing from the spirit or essential characteristics thereof. The forgoing implementations are therefore to be considered in all respects illustrative, rather than limiting of the invention.

CONCLUSION

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, e.g., to mean including but not limited to. Only the transitional phrases "consisting of and" consisting essentially of shall be closed or semi-closed transitional phrases, respectively, as set forth in the United States Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

What is claimed:

1. A system comprising one or more processors and a memory storing processor executable instructions, wherein execution of the instructions stored in the memory cause the one or more processors to:
   retrieve, from the memory, an optical coherence tomography (OCT) image of retina tissue;
   determine a location of a fovea in the OCT image;
   identify a transect from the OCT image a predetermined distance from the location of the fovea, wherein the transect comprises an array of intensity values through the retina tissue of the OCT image;
   generate a profile for the transect, the profile for the transect comprising at least one statistic of the array of intensity values; and
   classify the OCT image using the profile for the transect into one of a wet age-related macular degeneration (AMD) group, a dry AMD group, or a healthy group.

2. The system of claim 1, wherein execution of the instructions stored in the memory cause the one or more processor to preprocess the OCT image with at least one of down-sampling, de-noising, filtering, or flattening.

3. The system of claim 2, wherein the wherein execution of the instructions stored in the memory cause the one or more processors to filter the OCT image with a Frangi filter.

4. The system of claim 1, wherein execution of the instructions stored in the memory cause the one or more processors to:
   identify an outline of the of the retina tissue;
   calculate a derivative of the outline; and
   determine a location of a minimum of the derivative.

5. The system of claim 1, wherein execution of the instructions stored in the memory cause the one or more processors to extract a plurality of transects from the OCT image.

6. The system of claim 5, wherein execution of the instructions stored in the memory cause the one or more processors to generate the profile responsive to each of the plurality of transects.

7. The system of claim 5, wherein execution of the instructions stored in the memory cause the one or more processors to generate a respective profile for each of the plurality of transects.

8. The system of claim 1, wherein execution of the instructions stored in the memory cause the one or more processors to determine a number of times the profile crosses at least one threshold.

9. The system of claim 1, wherein execution of the instructions stored in the memory cause the one or more processors to classify the OCT image with at least one of a linear discriminant analysis (LDA), a k-nearest neighbor based algorithm, or a support vector machine.

10. A method comprising:
    retrieving, from a memory, an optical coherence tomography (OCT) image of retina tissue;
    determining a location of a fovea in the OCT image;
    identifying a transect from the OCT image a predetermined distance from the location of the fovea, wherein the transect comprises an array of intensity values through the retina tissue of the OCT image;

generating a profile for the transect, the profile for the transect comprising at least one statistic of the array of intensity values; and classifying the OCT image using the profile for the transect into one of a wet age-related macular degeneration (AMD) group, a dry AMD group, or a healthy group.

11. The method of claim 10, further comprising preprocessing the OCT image with at least one of a downsampling, a de-noising, a filtering, or a flattening algorithm.

12. The method of claim 11, further comprising filtering the OCT image with a Frangi filter.

13. The method of claim 10, further comprising:
identifying an outline of the of the retina tissue;
calculating a derivative of the outline; and
determining a location of a minimum of the derivative.

14. The method of claim 10, further comprising extracting a plurality of transects from the OCT image.

15. The method of claim 14, further comprising generating the profile responsive to each of the plurality of transects.

16. The method of claim 14, further comprising generating a respective profile for each of the plurality of transects.

17. The method of claim 10, further comprising determining a number of times the profile crosses at least one threshold.

18. The method of claim 10, further comprising classifying the OCT image with at least one of a linear discriminant analysis (LDA), a k-nearest neighbor based algorithm, or a support vector machine.

* * * * *